United States Patent
Snoble et al.

(10) Patent No.: US 7,514,588 B2
(45) Date of Patent: Apr. 7, 2009

(54) PURIFICATION OF ORGANIC SOLVENTS

(75) Inventors: Karel A. J. Snoble, Norton Shores, MI (US); Shihan Chen, Palatine, IL (US); Alexander M. Bershitsky, Glenview, IL (US); Russell W. Johnson, Elmhurst, IL (US)

(73) Assignee: Honeywell International Inc., Morristown, NJ (US)

(*) Notice: Subject to any disclaimer, the term of this patent is extended or adjusted under 35 U.S.C. 154(b) by 9 days.

(21) Appl. No.: 10/284,948

(22) Filed: Oct. 31, 2002

(65) Prior Publication Data

US 2003/0094417 A1 May 22, 2003

Related U.S. Application Data

(60) Provisional application No. 60/334,837, filed on Oct. 31, 2001.

(51) Int. Cl.
 *C07C 29/74* (2006.01)
(52) U.S. Cl. ...................................................... 568/917
(58) Field of Classification Search ................. 568/917
 See application file for complete search history.

(56) References Cited

U.S. PATENT DOCUMENTS

| | | | | |
|---|---|---|---|---|
| 1,593,304 A | * | 7/1926 | Johns | 568/917 |
| 2,647,150 A | * | 7/1953 | Askevold | 568/69 |
| 3,230,156 A | * | 1/1966 | Katzen | 203/37 |
| 3,408,267 A | * | 10/1968 | Miller et al. | 203/19 |
| 3,619,120 A | * | 11/1971 | Conlisk et al. | 8/142 |
| 4,263,407 A | | 4/1981 | Reed, Jr. | 521/33 |
| 4,465,875 A | * | 8/1984 | Greenbank et al. | 568/916 |
| 4,502,957 A | * | 3/1985 | Jehle et al. | 210/690 |
| 4,543,432 A | * | 9/1985 | Shih et al. | 568/917 |
| 4,839,331 A | | 6/1989 | Maroldo et al. | 502/416 |
| 5,726,118 A | | 3/1998 | Ivey et al. | 502/417 |
| 6,388,112 B1 | * | 5/2002 | Anevski | 554/191 |
| 6,417,412 B1 | * | 7/2002 | Kahn et al. | 568/917 |
| 6,733,637 B1 | * | 5/2004 | Burton et al. | 203/14 |

FOREIGN PATENT DOCUMENTS

JP 08291091 A * 11/1996

OTHER PUBLICATIONS

Tu, Jieying; Meng, Mingbao Preparation of pure organic solvents for spectrophotometric analysis Huanjing Baohu (Beijing, China) (1984), (1), 27-8.*

Tu, Jieyang; Meng, Mingbao Preparation of pure organic solvents for spectrophotometric analysis Huanjing Baohu (Beijing, China) 1984, (1), 27-8. (abstract enclosed).*

Schweiger, Thomas A.J., "Effects of Water Residues on Solvent Adsorption Cycles," *Ind. Eng. Chem. Res.*, (1995) 34, 283-287.

Jieying et al., Environmental Protection, 1984, 27 *et seq*.

* cited by examiner

*Primary Examiner*—Elvis O Price
(74) *Attorney, Agent, or Firm*—Erika S. Wilson (57) ABSTRACT

The present invention is directed to processes for producing a high purity organic solvent from a crude organic solvent comprising providing a stream of crude organic solvent comprising a first amount of at least one impurity and adsorbing at least one impurity contained in said crude organic solvent onto an adsorbent to produce a purified organic solvent comprising a second amount of impurities, the second amount of impurities being less than the first amount of impurities.

25 Claims, 4 Drawing Sheets

PURIFICATION OF ORGANIC SOLVENTS

CROSS-REFERENCE TO RELATED APPLICATION

This application claims priority to U.S. Provisional Application Ser. No. 60/334,837 filed with the United States Patent and Trademark Office on Oct. 31, 2001.

FIELD OF THE INVENTION

The present invention relates to methods of obtaining high purity organic solvents. In particular, the present invention relates to methods of obtaining high purity organic solvents using adsorption techniques.

BACKGROUND OF THE INVENTION

The manufacture of organic solvents in commercial quantities often results in the production of crude solvents containing at least some level, and often relatively high levels, of impurities. Although such crude solvents are frequently acceptable for certain applications, applicants have recognized that the impurity level in many commercially available sources of organic solvents, particularly methanol, creates significant problems in other applications.

Accordingly, applicants have heretofore attempted to use distillation techniques to remove impurities from a wide variety of commercially available crude methanols to produce methanol having suitably low impurity levels. Unfortunately, applicants have discovered that distillation is not a particularly effective method for removing impurities for a number of reasons. One reason, for example, is that many impurities found in commercial methanols have boiling points that are similar to the boiling point of methanol, thus making them particularly difficult to remove via distillation.

In addition, applicants have discovered that the vast majority of commercially available crude methanols contain levels of impurities so high that it is extremely difficult, if not impossible, to sufficiently lower the amount of impurities via conventional distillation to acceptable levels. Sources of the impurities found in commercially available crude methanol likely include inefficiency at the production site and/or contamination during product handling (for example, cross-contamination from transfer lines, barges, trucks, rail cars, intermediate storage tanks, etc). Accordingly, crude methanols more suitable for distillation could be produced commercially by increasing efficiency at the production site and in product handling. However, such changes would be extremely costly and difficult to control.

Therefore, applicants have developed the present process which allows for the production of high purity solvents from crude solvents.

DETAILED DESCRIPTION OF THE INVENTION

The present inventors have discovered a process for removing impurities from an organic solvent by contacting the solvent with an adsorbent. Applicants have discovered that adsorption, either alone or in combination with other separation techniques, is capable of producing, from a wide variety of sources of relatively impure solvents, an organic solvent having a relatively low impurity level that would be costly and difficult, if not impossible, to achieve using prior art processes.

The present invention thus comprises removing impurities from a crude organic solvent to produce a purified solvent. As used herein, the term "crude organic solvent" refers to an organic solvent-containing material that contains a level of at least one impurity that is greater than the level of impurity desired or allowable in the organic solvent for a given application or intended use. Those skilled in the art will appreciate that the amount of a given impurity desired or allowable will vary widely depending on numerous factors, including the specific impurity(ies) involved and the expected use of the material after purification. It is expected that any and all of a wide range of crude organic solvents can be processed according to the present invention to produce purified solvents of various, relatively low levels of impurities.

For example, many industrial applications require the use of alcohols, such as methanol and isopropanol, having very low levels of impurities. Often such applications require alcohols having less than 1 wt % and preferably less than 0.1 wt % impurities based on the total weight of the solvent.

Those of skill in the art will appreciate that one standard measure of solvent impurities at such low levels is based on the ultraviolet (UV) absorption of the solvents. In general, a solvent placed in a sample cell of a given path length and subjected to UV radiation at a given wavelength will exhibit a level of UV absorbance. As the level of impurities in the solvent increases, the level of UV absorbance tends to increase as well. Accordingly, a maximum allowable UV absorbance measurement for a given solvent corresponds to a maximum allowable level of impurities allowable in the solvent. For example, in many applications of high purity methanol and/or isopropanol, it is desirable to have a UV absorbtion of less than about 1.0 Absorption Unit Full Scale ("AUFS"), preferably less than about 0.9 AUFS, and more preferably less than about 0.8 AUFS for a 5 cm cell at 225 nm. In addition, it is preferable to have a UV absorption of less than about 0.3, more preferably less than about 0.2, and even more preferably less than about 0.1 AUFS for a 5 cm cell at 250 nm; less than about 0.05, more preferably less than about 0.04, and even more preferably less than about 0.025 AUFS for a 5 cm cell at 300 and 400 nm. All the above UW absorption measurements were measured using a Varian Cary Model 4E UV-Visable Spectrometer.

For embodiments involving methanol, another standard measure of solvent purity is absorbance measured via the Tennesee-Eastman HPLC method. As will be recognized by those of skill in the art, this method employs gradient to concentrate, elute, and measure the level of impurities contained in an organic solvent via UV adsorbtion. For example, in certain preferred embodiments, the level of impurities in methanol are measured by initially running a solution of 95 wt % water and 5 wt % methanol through a C-8 reverse phase column and gradually changing the proportion of solvents to 100 wt % methanol and 0 wt % water over about 20 minutes. After the 100 wt % methanol is run through the column for some time, the gradient is gradually lowered back to 95 wt % water and 5 wt % methanol. As the solvent samples are eluted from the column, they pass in a continuous stream through a detector wherein the UV adsorption of the stream at one or more wavelengths is measured. In general, maximum levels of UV adsorbence at each UV wavelength correspond to maximum levels of impurities allowed in the solvent, as measured via the TE process. In many high purity methanol applications, it is desirable to have a TE absorption measurement of less than about 0.0090, preferably less than about 0.0070, and more preferably less than about 0.0050 AUFS at 220 nm, and a measurement of less than about 0.0050, preferably less than about 0.0030, and more preferably less than about 0.0010 AUFS at 254 nm.

In general, therefore, in embodiments of the present invention comprising the production of purified methanol and/or isopropanol, it is preferred that the crude solvent to be purified fails to satisfy one or more of the following absorption criteria: a UV absorption for a 5 cm cell of less than about 0.8 AUFS at 225 nm, less than about 0.1 AUFS at 250 nm, and less than about 0.025 AUFS at 300 and 400 nm. For embodiments comprising the purification of methanol, it is even more preferred that the crude methanol to be purified fails to satisfy one or more of the following absorption criteria: a UV absorption for a 5 cm cell of less than about 0.8 AUFS at 225 nm, less than about 0.1 AUFS at 250 nm, and less than about 0.025 AUFS at 300 and 400 nm and a Tennessee-Eastman absorbance of less than about 0.0050 AUFS at 220 nm and about 0.0010 AUFS at 254 nm. It is contemplated, however, that the present invention can be frequently utilized to its best advantage for embodiments in which the crude methanol fails to satisfy one or more of the following absorption criteria: a Tennessee-Eastman absorbance of less than about 0.2 AUFS at 220 nm and a Tennessee-Eastman absorbance of less than about 0.2 AUFS at 254 nm. As will be appreciated, it was not economically feasible to employ crude methanols having such high levels of impurities to obtain purified methanol using prior art processes.

The first step according to the preferred embodiments of the present invention is to provide a crude organic solvent containing a first amount of at least one impurity.

Any of a wide range of organic solvents can be provided according to the present invention. Suitable solvents include: alcohols, and preferably $C_1$-$C_5$ alcohols, including, $C_1$-$C_3$ alcohols such as methanol, ethanol, isopropanol, and the like; ketone carbonyls, including, acetone, methyl isobutyl ketone, and the like; esters, including, ethyl acetate, n-butyl acetate and the like; acetonitrile; and the like.

In certain applications, the providing step comprises simply obtaining from commercially available sources crude organic solvent in the amount and, if applicable, at the rate required for the desired purpose. Many of the organic solvents suitable for use in the present invention as crude solvents are available commercially. For example, crude methanol is available commercially from Methanex, Ashland, Mitsubishi, Celanese, Equistar, and other commercial providers. Suitable commercially available methanol and isopropanols commonly have UV absorptions of greater than about 1.0 AUFS at 225 nm, about 0.3 AUFS at 250 nm, and about 0.05 AUFS at 300 and 400 nm for 5 cm cell samples. Commercially available methanol and/or isopropanols containing higher or lower levels of impurities may also be purified.

In certain embodiments, the crude organic solvent is provided from and/or through any of a wide range of storage or containment apparatus according to the present invention. Examples of suitable storage and/or containment apparatus include feed or storage bottles and tanks, transfer lines, barges, trucks, rail cars, combinations of two or more thereof, and the like.

Alternatively, the crude organic solvent may be provided directly to the present purification process as part of an integrated organic solvent production facility. Present manufacturing processes of solvents, for example, methanol, produce crude methanol streams containing varying levels of impurity. It is contemplated that any of a wide range of such crude streams may be provided according to the present invention.

The step of purifying the crude organic solvent preferably comprises removing impurities from the solvent by adsorbing the impurities on an adsorbent.

Any of a wide range of adsorbents are suitable for use in the present invention. For example, suitable adsorbents include activated carbon, synthetic carbons, synthetic adsorbents, inorganic molecular sieves, and the like. As used herein, the term "activated carbon" is given its commonly understood meaning to those of ordinary skill in the art. In general, activated carbon is understood to be a relatively complex, twisted network of defective carbon layer planes, cross linked by aliphatic bridging groups, and as described in U.S. Pat. No. 5,726,118—Ivy, et al., which is incorporated herein by reference. An important physical characteristics of activated carbon is that it possesses an internal pore structure having a vast internal surface area. Many commercially available forms of activated carbon have surface areas in the range of 500-2000 meters squared per gram ($m^2$/g) with some surface areas being reported as high as 3500-5000 $m^2$/g. It is contemplated that activated carbon having surface areas in the ranges indicated above will be adaptable for use in accordance with the present invention. Certain preferred activated carbons include those having a surface area of about 1000 to about 2000 $m^2$/g. In certain embodiments, it is more preferred to use activated carbons having a surface area of about 1400 to about 1800 $m^2$/g. Another important physical characteristic of an activated carbon is its pore volume. Certain preferred activated carbons include those having a pore volume of about 0.5 to about 1.5 milliliters per gram (ml/g), preferably about 1 to about 1.5 ml/g, and more preferably about 1 to about 1.2 ml/g for pores up to 1000 angstroms. In certain embodiments, it is further preferred to use an activated carbon having a trace capacity number of about 16 milligrams per cubic centimeter (mg/cc) or greater, and an iodine number of about 850 milligrams per gram (mg/g) or greater.

As used herein, the term "synthetic adsorbent" refers generally to polymeric adsorbent materials known in the art, often comprising resin-derived synthetic carbons, such as, for example, Ambersorb 572, as well as, homopolymers and/or copolymers of acrylic, vinyl, and/or styrene monomers, and the like, described in U.S. Pat. Nos. 4,839,331 and 4,263,407, both of which are incorporated herein by reference. Certain preferred synthetic adsorbents include synthetic carbons having a surface area of from about 500 to about 2000 meters squared per gram ($m^2$/g), more preferably from about 1000 to about 1500 $m^2$/g, and even more preferably about 1100 $m^2$/g. Preferred synthetic adsorbents also include synthetic carbons exhibiting pore volumes as follows: pores of less than about 20 angstroms having a pore volume of from about 0.8 to about 0.2 ml/g, preferably about 0.6 to about 0.3 ml/g, and more preferably about 0.41 ml/g; pores of from about 20 angstroms to about 500 angstroms having a pore volume of from about 0.5 to about 0.1 ml/g, preferably about 0.4 to about 0.15 ml/g, and more preferably about 0.19 ml/g; pores of greater than about 500 angstroms having a pore volume of from about 0.5 to about 0.1 ml/g, preferably about 0.4 to about 0.15 ml/g, and more preferably about 0.19 ml/g.

A wide range of adsorbents suitable for use in accordance with the present invention are available commercially from numerous sources. For example, suitable activated carbon adsorbents include, Nuchar RGC (available from Westvaco), Calgon Filtrasorb 600 and Calgon SGL (available from Calgon), Norit and Norit ROX 0.8 (available from Norit Americas, Inc.).

In certain embodiments, it is preferable to use a mixture of two or more types of adsorbents, especially two or more activated carbons, as an absorbent in the present methods. Although applicants do not wish to be bound by or to any particular theory of operation, it is believed that using more than one type of adsorbent, and in particular using a mixture of two or more carbon adsorbents, has a synergistic effect, allowing for the removal of greater amounts of impurities from crude organic solvents as compared to certain single carbon adsorbents. In view of the teachings contained herein, those of skill in the art will be readily able to determine suitable mixtures of activated carbons for use in removing various impurities from organic solvents according to the present invention without undue experimentation.

According to preferred embodiments, the adsorbent, which is preferably a pre-conditioned adsorbent, is packed into a vessel, such as a column, to form an adsorbent bed. As used herein, the term "pre-conditioned" refers generally to the process of wetting the adsorbent with solvent to degas the adsorbent and to control the exotherm of adsorption. As will be recognized by those of skill in the art, upon wetting an adsorbent for the first time, air adsorbed within the adsorbent tends to evolve and a substantial amount of heat of adsorption is generated. The generation of heat may cause the wetting solvent to boil under atmospheric pressure and further evolve gas from the adsorbent/solvent mixture. Therefore, provisions must be provided to remove the gases from the adsorbent bed as they are generated during column preparation.

According to certain embodiments, especially those involving large-scale operation, it is preferable to pre-condition the adsorbent outside of the containment vessel to safely manage the degassing and exotherm. In other embodiments, any of a wide number of methods for pre-conditioning an adsorbent inside a column may also be used. For example, a solvent condenser may be connected to the adsorbent column or columns to help regulate the evolution of gas during pre-conditioning. For embodiments involving small scale purifications, the column may be packed dry, then wetted. In general, the adsorbent bed is pre-conditioned using either the crude organic solvent, previously-purified organic solvent, or combinations thereof. According to certain preferred embodiments, the absorbent bed is pre-conditioned using crude solvent.

After the adsorbent has been pre-conditioned, a stream of crude organic solvent is preferably contacted by, and even more preferably, passed through a bed of adsorbent. The flow rate at which the organic solvent is passed through the adsorbent bed can be readily determined by those skilled in the art based on the size of the adsorbent bed being used, which in turn is based on the other particular process and product requirements. The size of a adsorbent bed to be employed, and the amount of adsorbent to be used, with a given process can therefore be readily determined by one skilled in the art without undue experimentation. The flow rate used will also depend on the desired purity level. Higher purity levels require lower flow rates to increase the residence time of the solvent on the adsorbent to ensure thorough adsorption of impurities onto the adsorbent. According to certain preferred embodiments, the flow rate is adjusted such that the superficial velocity of the solvent is from about 1 to about 5 meters per hour (m/hr), preferably from about 2 to about 4 m/hr, and more preferably, about 3 m/hr.

According to certain preferred embodiments, the present process comprises using two or more adsorbent beds arranged in series to remove impurities from crude organic solvent. Generally, the two or more adsorbent beds may be of the same or different sizes and may comprise the same or different adsorbents. In certain preferred embodiments, the present methods comprises the use of a first "main" column to remove a majority of the impurities from a crude solvent passed therethrough, followed by the use of a second "polishing" column to remove a further quantity of impurities from the organic solvent. In other preferred embodiments, the two or more adsorbent beds are arranged in a dual carbon bed system.

As the process continues, the impurities will generally build up in the adsorbent bed. Eventually the bed begins to become saturated with the impurities. When this occurs, the level of impurities in the finished product begins to increase, at which time the adsorbent is either replaced or regenerated.

Replacement or regeneration is preferably performed before occurrence of a "breakthrough" in the impurity level for embodiments involving a single adsorbent bed or a parallel bed arrangement. For embodiments involving a single adsorbent bed, it is contemplated that the bed replacement may comprise removing the adsorbent bed from the column in which it is housed and introducing pre-conditioned, newly regenerated or virgin adsorbent into the same column. Alternatively, the entire column may be replaced with a new column containing pre-conditioned, newly regenerated or virgin adsorbent.

For embodiments in which two or more beds are used in a series arrangement, it is contemplated that the level of impurity at the exit of the first bed could well exceed the "breakthrough" level since the one or more subsequent bed(s) in the series would act as buffer zones to ensure that the partially purified solvent leaving the first bed is purified to the desired impurity level. In such embodiments, the first bed is generally taken off-line and a newly regenerated bed or bed of virgin adsorbent would be introduced to the series arrangement. In general, a "breakthrough" is deemed to have occurred when the level of the impurity in the purified stream leaving the adsorption step exceeds the predefined maximum amount of impurity for the desired product. For example, when a product has a predetermined maximum impurity of 10 ppm impurity, then the breakthrough concentration is set at 10 ppm. When a product with less than 1 ppm impurity is desired, then the breakthrough concentration is set at 1 ppm, and so forth.

In embodiments involving regeneration, the adsorbent is regenerated by well-understood, conventional means. For example, activated carbon may be washed with water or dilute aqueous potassium hydroxide, rinsed with water to remove potassium hydroxide (as needed) and then re-used. The activated carbon is preferably dried before re-use. The potassium hydroxide solution may be re-used until it contains a phosphate concentration that interferes with the regeneration process, which is readily identified by those skilled in the art, at which point the impurities are preferably disposed of in a commercially and environmentally acceptable manner. In such a process the crude organic solvent flow is alternated between two carbon beds, with one adsorbent bed being regenerated while the other is employed for purification. Adsorbent bed regeneration processes are disclosed, for example, in Japanese Patent No. JP 10151344 (date Jun. 9, 1998) and "*Effects of Water Residues on Solvent Adsorption Cycles,*" Schweiger, Thomas A. J., Ind. Eng. Chem. Res. (1995), 34(1), 283-7, each of which is incorporated herein by reference.

The adsorption step of the present invention may be conducted under any suitable conditions. For methanol, the adsorption step is preferably carried out at temperatures of from about 0° C. to about 45° C., preferably from about 10° C. to about 35° C., and more preferably at about room temperature.

In a preferred embodiment, the present methods further comprise the step of separating impurities from a crude organic solvent by distillation, which can occur before and/or after the adsorbtion step. It is generally preferred, however, that the present process include a distillation step after the adsorbtion step. Any of a wide range of known distillation methods can be used according to the present invention, including, for example, the distillation methods described in: Job Training Systems, Inc. (Unionville, Pa.) "Distillation Basic Principles Course No. 116 (1985 ed.) and K. B. Wiberg, "Laboratory Technique in Organic Chemistry," McGraw-Hill Book Co. Inc. (1960) (New York) (Library of Congress Catalog Card Number 59-11950), both of which are incorporated herein by reference. Those of skill in the art will be able to readily adapt such distillation methods for use in the process of the present invention.

Figure 1:
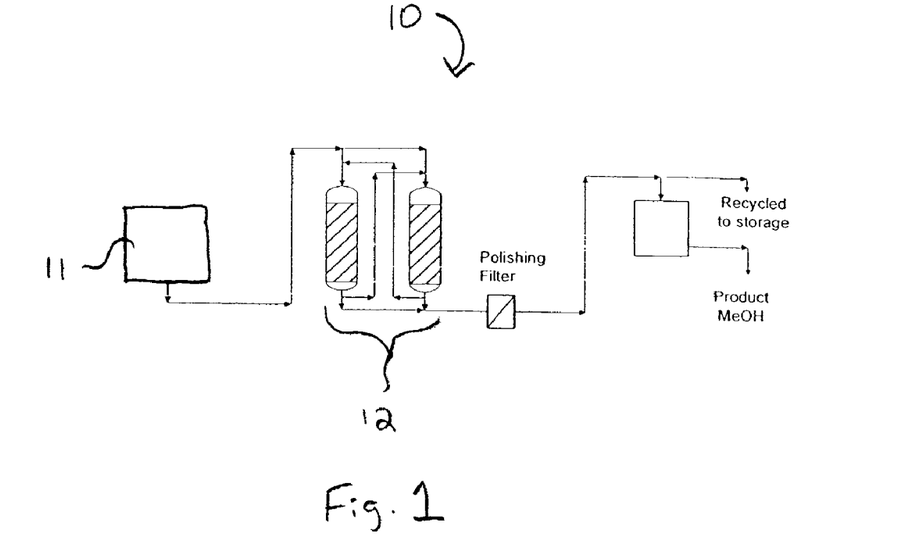
FIG. 1 is a diagram of an adsorbtion system for use according to certain embodiments of the present invention.
Figure 2:
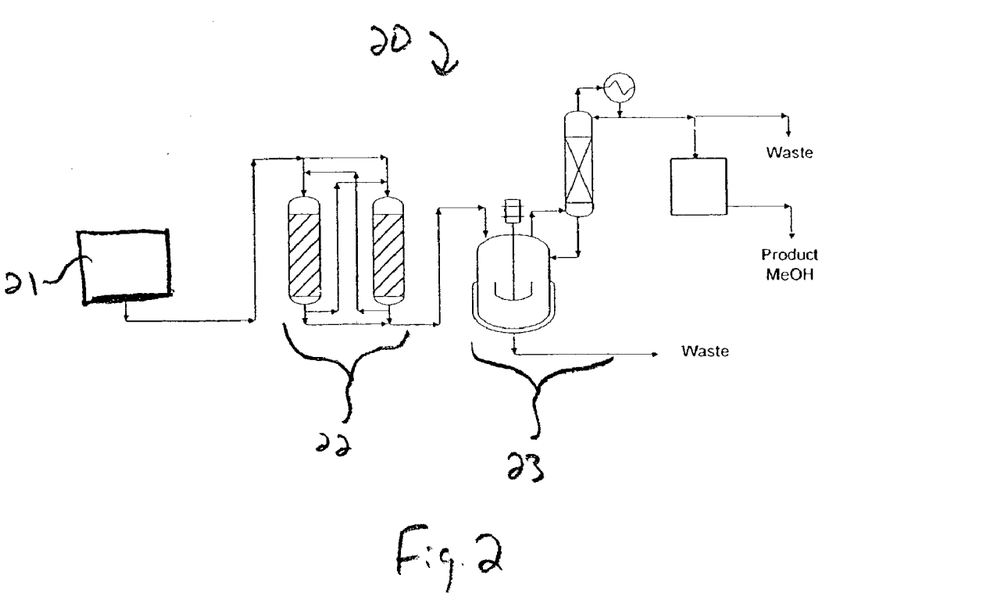
FIG. 2 is a diagram of an adsorbtion/distillation system for use according to certain embodiments of the present invention.
Figure 3:
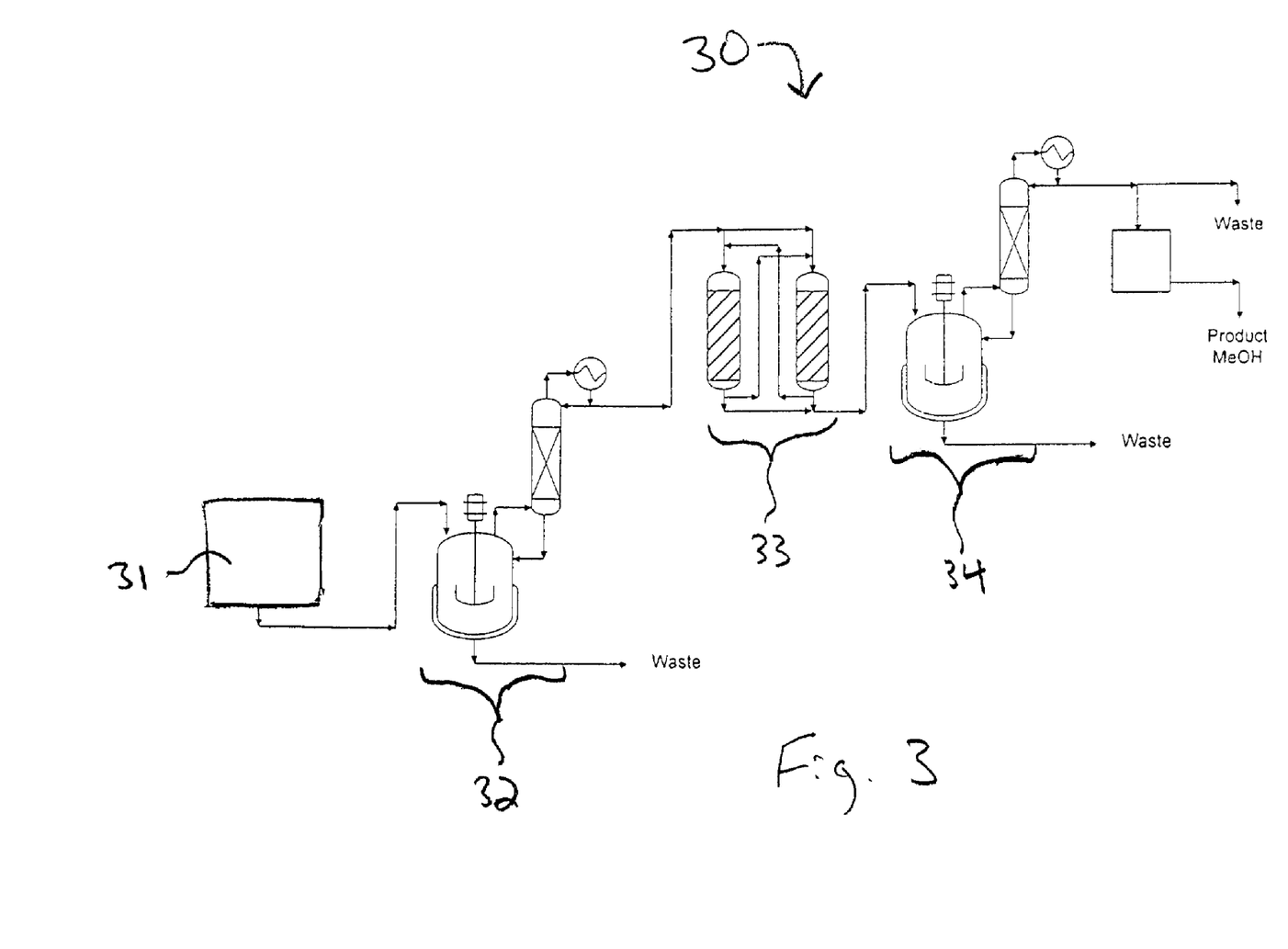
FIG. 3 is a diagram of an adsorbtion/distillation system for use according to certain other embodiments of the present invention.
Figure 4:
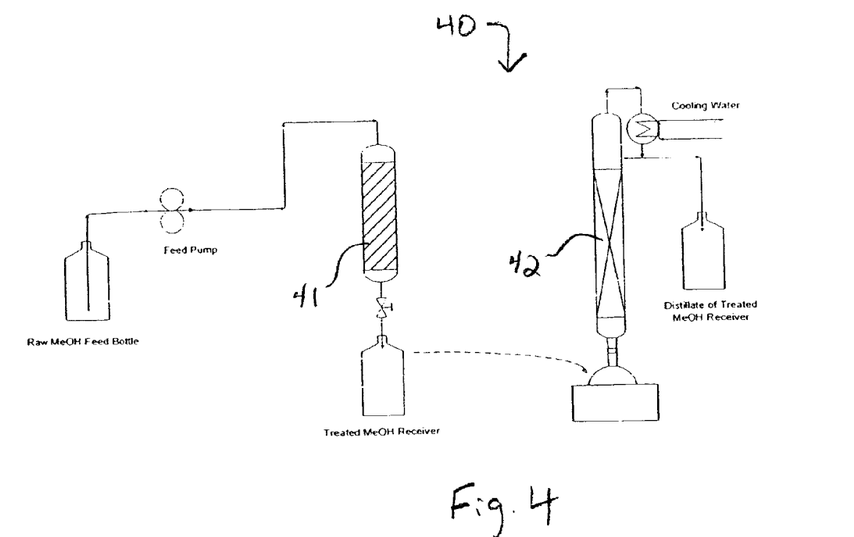
FIG. 4 is a diagram of a batch adsorbtion/distillation system for use according to certain embodiments of the present invention.

The methods of the present invention include both continuous and batch processes. Any apparatus or combination of apparatus suitable for use in conducting one or more adsorption and, optionally, distillation steps according to the present invention in a continuous or batch system may be used. By way of example, FIGS. 1-3 show continuous systems suitable for use according to certain embodiments of the present invention. FIG. 1 shows a continuous system 10 comprising a crude solvent storage/containment device 11 connected to a system of adsorbtion columns 12. In processes using the system shown in FIG. 1, crude solvent is provided from device 11 to system 12 wherein impurities within the solvent are adsorbed to produce purified solvent. FIG. 2 shows a continuous system 20 comprising a crude solvent storage device 21 connected to a system of adsorbtion columns 22 which, in turn, is connected to a distillation column 23. In such embodiments, solvent is provided from device 21 to the adsorbtion system 22 for adsorbtion and subsequently distilled via distillation column 23 to produce purified solvent. FIG. 3 shows a continuous system 30 comprising a crude solvent storage device 31 connected to a distillation column 32 which is connected to an adsorbtion system 33 which, in turn, is connected to a second distillation column 34. In such embodiments, crude solvent provided form device 31 is distilled, then passed through the adsorbtion system 33 and distilled again to proved purified solvent. FIG. 4 shows an exemplary batch system set up 40 comprising an adsorbtion column 41 and a distillation column 42 for use according to certain embodiments of the present invention.

As shown above, in certain embodiments, the adsorbtion and distillation steps of the present processes are connected in series such that the solvent product of one or more of the adsorbtion or distillation steps is provided directly to the next adsorbtion or distillation step for further purification. In certain other embodiments, the present processes comprise the step of storing the solvent product of one or more intermediate adsorption or distillation steps prior to providing such product to a subsequent adsorbtion or distillation step to produce purified solvent. For example, FIGS. 5 and 6 show continuous systems for use according to such embodiments.

Figure 5:
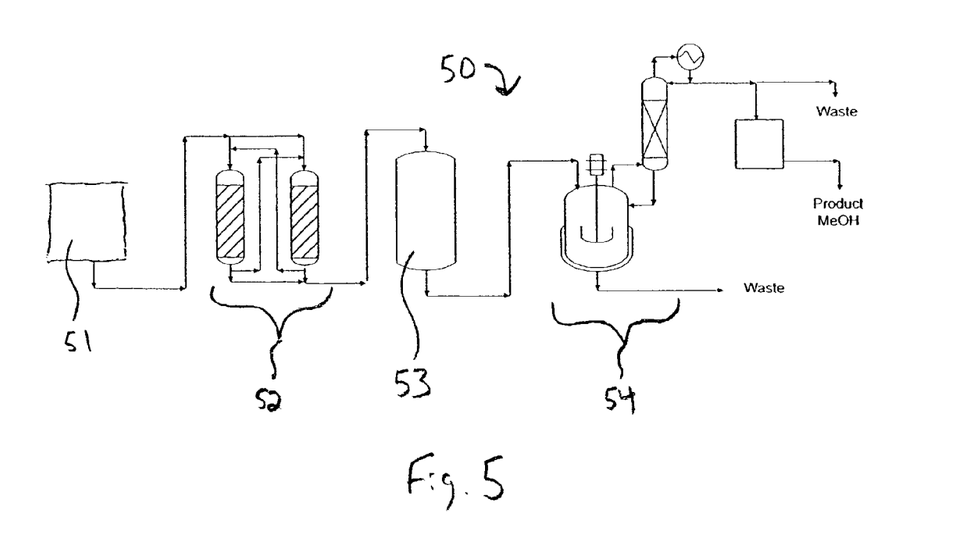
FIG. 5 is a diagram of an adsorbtion/distillation system for use according to certain embodiments of the present invention.
Figure 6:
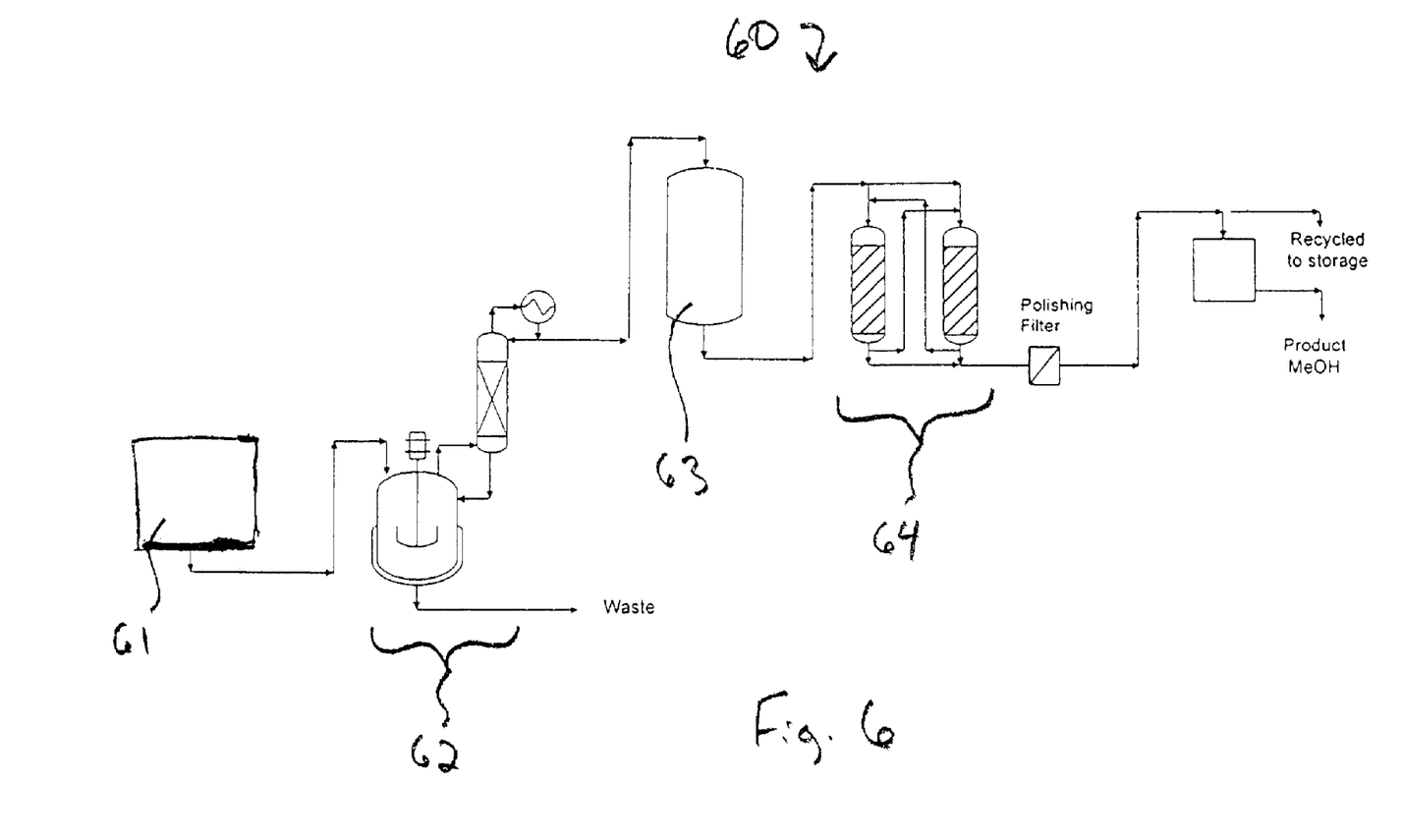
FIG. 6 is a diagram of an adsorbtion/distillation system for use according to certain other embodiments of the present invention.

FIG. 5 shows a continuous system 50 comprising a crude solvent storage device 51 connected to an adsorbtion column system 52. Adsorbtion system 52 is connected to a second solvent storage device 53 which, in turn, is connected to a distillation column 54. In such embodiments, crude methanol is provided from device 51 to system 52 wherein impurities within the solvent are adsorbed to produce an adsorbtion solvent product. The adsorbtion solvent product is then provided to storage device 53 wherein it is stored for a suitable period of time. After such time, the adsorbtion solvent product is provided to distillation column 54 wherein it is distilled to produce purified solvent. FIG. 6 shows a system 60 comprising a storage device 61, a distillation column 62, a second storage device 63 and an adsorbtion column system 64 wherein crude solvent provided from device 61 is distilled, stored for a suitable period of time, and then run through system 64 to produce purified solvent.

Any suitable storage or containment devices described hereinabove can be used to store the intermediate solvent products according to the present invention. As will be recognized by those of skill the art, the amount of time suitable for storing an intermediate solvent product for any given application will depend on a number of factors including the solvent being purified and the level of purity desired. In general, a solvent may be stored according to the present processes for as long as one or more hours, days, weeks, months, and even years. In light of the disclosure herein, those of skill in the art will be readily able to incorporate a storage step into processes according to the present invention.

The present invention may also be performed as part of a process in which purified solvent is added to a chemical reaction, preferably as part of a commercial process. That is, an in-line purification process may be provided as part of a step to supply high purity organic solvent to a chemical reaction.

EXAMPLES

The following examples illustrate a preferred process by which impurities are removed from a crude organic solvent but do not in any way restrict the effective scope of the invention.

Example 1

Sixty eight (68) cubic centimeters of Ambersorb 572 adsorbent is soaked in 50 milliliters (ml) of crude methanol for 15 min. The crude methanol is decanted from the adsorbent and the adsorbent is packed into a glass column. Crude methanol (500 ml) is flowed through the glass column at a rate of about 3 ml/min and collected for UV and Tennessee-Eastman (TE) analysis. The collected methanol has a UV adsorption of less than about 0.8 AUFS at 225 nm, less than about 0.1 AUFS at 250 nm, and less than about 0.025 AUFS at 300 and 400 nm and the Tennessee-Eastman absorbance is less than about 0.0050 AUFS at 220 nm and less than about 0.0010 AUFS at 254 nm.

Example 2

Sixty eight (68) cubic centimeters of Ambersorb 572 adsorbent is soaked in 50 milliliters (ml) of crude methanol for 15 min. The crude methanol is decanted from the adsorbent and the adsorbent is packed into a glass column. Crude methanol (500 ml) is flowed through the glass column at a rate of about 3 ml/min and collected. The collected methanol is distilled to produce a distilled methanol product. The distilled methanol product is analyzed via TE analysis and exhibits adsorption of less than about 0.0050 AUFS at 220 nm and less than about 0.0010 AUFS at 254 nm.

Additional crude methanol is passed through the column and collected in 500 ml samples that are distilled and then analyzed via TE analysis until the collected samples exhibit absorption greater than 0.0050 AUFS at 220 nm and 0.0010 AUFS at 254 nm. The adsorbent in the column is then discarded and the column is repacked with 68 cubic centimeters of pre-conditioned, virgin Ambersorb 572. After repacking, a 500 ml sample of crude methanol is flowed through the column and collected. The sample is distilled and analyzed via TE method. The distilled sample exhibits adsorption of less than about 0.0050 AUFS at 220 nm and less than about 0.0010 AUFS at 254 nm.

Example 3

To 27 grams of an adsorbent contained in a beaker is added sufficient methanol to cover the adsorbent. The adsorbent and methanol is mixed for about 9 minutes and then allowed to settle for 15 minutes. The methanol is then decanted from the adsorbent and water is added to the adsorbent. The water and adsorbent is stirred for about 1.5 minutes and allowed to settle for 10 minutes after which the water is decanted from the adsorbent. Fifty (50) ml of methanol is added to the adsorbent and the methanol/adsorbent slurry is added to a column. After some initial methanol is run through the column, 500 ml of crude methanol is passed through the column at about 3.7 ml/min and collected. The collected sample is heated to reflux and a 10 ml sample of distilled methanol is pulled. Then the majority of distilled methanol is collected.

Example 4

17.1 kg of an activated carbon adsorbent is mixed with 400 liters of crude methanol and the methanol is subsequently decanted from the adsorbent. The adsorbent is added to an 8"×84" stainless steel column having a volume of 69 liters. About 2500 liters of crude methanol is passed through the column at a flow rate of about 1.77 liters/min and a superficial velocity of about 3.28 m/hr and collected. The collected methanol is analyzed using the TE method and exhibits adsorption of less than about 0.0050 AUFS at 220 nm and less than about 0.0010 AUFS at 254 nm.

Example 5

17.3 g of an activated carbon adsorbent is mixed with crude methanol and the methanol is subsequently decanted from the adsorbent. The adsorbent is added to an 0.67"×10" glass column having a volume of 57 ml. About 1500 liters of crude methanol is passed through the column at a flow rate of about 4-7 ml/min and a superficial velocity of about 1-2 m/hr and collected. The collected methanol is analyzed using the TE method and exhibits adsorption of less than about 0.0050 AUFS at 220 nm and less than about 0.0010 AUFS at 254 nm.

Example 6

A combined column comprising a main column containing a first preconditioned activated carbon adsorbent linked in series to a second column containing a second preconditioned activated carbon adsorbent is prepared. Crude methanol is passed through the combined column at a flow rate of about 6 ml/min and a superficial velocity of about 3.9 m/hr and collected. The collected sample is heated to reflux and a sample of distilled methanol is pulled. The distilled methanol is analyzed using the TE method and exhibits adsorption of less than about 0.0050 AUFS at 220 nm and less than about 0.0010 AUFS at 254 nm.

Example 7

A combined column comprising a main column containing a preconditioned activated carbon adsorbent linked in series to a second column containing preconditioned Ambersorb 572 is prepared. Crude methanol is passed through the combined column at a flow rate of about 6 ml/min and a superficial velocity of about 3.9 m/hr and collected. The collected sample is heated to reflux and a sample of distilled methanol is pulled. The distilled methanol is analyzed using the TE method and exhibits adsorption of less than about 0.0050 AUFS at 220 nm and less than about 0.0010 AUFS at 254 nm.

Example 8

A column containing a preconditioned Calgon F600 adsorbent is prepared. Crude isopropanol is passed through the combined column at a flow rate of about 6 ml/min and a superficial velocity of about 3.9 m/hr and collected. The collected sample is heated to reflux and a sample of distilled isopropanol is pulled. The distilled sample exhibits adsorption of less than about 0.0050 AUFS at 220 nm and less than about 0.0010 AUFS at 254 nm.

Example 9

A combined column comprising a main column containing a first preconditioned activated carbon adsorbent linked in series to a second column containing a second preconditioned activated carbon adsorbent is prepared. Crude organic solvent is passed through the combined column at a flow rate of about 6 ml/min and a superficial velocity of about 3.9 m/hr and collected. The collected sample is heated to reflux and a sample of distilled solvent is pulled. The distilled solvent is analyzed using the TE method and exhibits sufficient purity for its intended application.

What is claimed is:

1. A process for producing a high purity organic solvent from a crude organic solvent comprising:
   providing a stream of a crude organic solvent comprising a first amount of at least one UV absorbing impurity;
   contacting said crude organic solvent stream with an adsorbent comprising a first porous material having a pore volume from about 0.1 to about 0.8 ml/g and a second porous material having a pore volume from about 1.0 to about 1.5 ml/g, wherein said first and second porous materials are independently selected from the group consisting of activated carbons, synthetic carbons, synthetic adsorbents, and inorganic molecular sieves; and
   adsorbing at least one dissolved UV absorbing impurity contained in said crude organic solvent onto said adsorbent to produce a purified organic solvent comprising a second amount of UV absorbing impurities, the second amount of impurities being less than the first amount of impurities;
   wherein said organic solvent is selected from the group consisting of $C_1$-$C_3$ alcohols, ketone carbonyls, esters, and acetonitrile.

2. The process of claim 1 wherein said organic solvent is selected from the group consisting of, acetone, methyl isobutyl ketone, ethyl acetate, n-butyl acetate and acetonitrile.

3. The process of claim 1 wherein said organic solvent is a $C_1$-$C_3$ alcohol.

4. The process of claim 1 wherein said crude organic solvent is a crude $C_1$-$C_3$ alcohol that fails to satisfy one or more of the following absorption criteria: a UV absorption for a 5 cm cell of less than about 0.8 AUFS at 225 nm, less than about 0.1 AUFS at 250 nm, and less than about 0.025 AUFS at 300 and 400 nm.

5. The process of claim 1 wherein said crude organic solvent is a crude $C_1$-$C_3$ alcohol that fails to satisfy one or more of the following absorption criteria: a UV absorption for a 5 cm cell of less than about 0.8 AUFS at 225 nm, less than about 0.1 AUFS at 250 nm, and less than about 0.025 AUFS at 300 and 400 nm, a Tennessee-Eastman absorbance of less than about 0.0050 AUFS at 220 nm and a Tennessee-Eastman absorbance less than about 0.0010 AUFS at 254 nm.

6. The process of claim 4 wherein said crude alcohol fails to satisfy one or more of the following absorption criteria: a UV absorption for a 5 cm cell of less than about 1.0 AUFS at 225 nm, less than about 0.3 AUFS at 250 nm, less than about 0.05 AUFS at 300 and 400 nm.

7. The process of claim 5 wherein said crude alcohol fails to satisfy one or more of the following absorption criteria: a UV absorption for a 5 cm cell of less than about 1.0 AUFS at 225 nm, less than about 0.3 AUFS at 250 nm, less than about 0.05 AUFS at 300 and 400 nm, a Tennessee-Eastman absorbance of less than about 0.0090 AUFS at 220 nm and a Tennessee-Eastman absorbance of less than about 0.0050 AUFS at 254 nm.

8. The process of claim 5 wherein said crude alcohol fails to satisfy one or more of the following absorption criteria: a Tennessee-Eastman absorbance of less than about 0.2 AUFS at 220 nm and a Tennessee-Eastman absorbance of less than about 0.2 AUFS at 254 nm.

9. The process of claim 4 wherein said purified alcohol meets the following criteria: a UV absorption for a 5 cm cell of less than about 1.0 AUFS at 225 nm, less than about 0.3 AUFS at 250 nm, less than about 0.05 AUFS at 300 and 400 nm.

10. The process of claim 9 wherein said purified alcohol meets the following criteria: a Tennessee-Eastman absorbance of less than about 0.0090 AUFS at 220 nm and a Tennessee-Eastman absorbance of less than about 0.0050 AUFS at 254 nm.

11. The process of claim 6 wherein said purified organic solvent is a purified $C_1$-$C_3$ alcohol that meets the following criteria: a UV absorption for a 5 cm cell of less than about 0.8 AUFS at 225 nm, less than about 0.1 AUFS at 250 nm, and less than about 0.025 AUFS at 300 and 400 nm.

12. The process of claim 11 wherein said purified organic solvent is a purified $C_1$-$C_3$ alcohol that meets the following criteria: a Tennessee-Eastman absorbance of less than about 0.0050 AUFS at 220 nm and a Tennessee-Eastman absorbance of less than about 0.0010 AUFS at 254 nm.

13. The process of claim 1 wherein said adsorbent comprises at least one activated carbon.

14. The process of claim 13 wherein said adsorbent further comprises at least one synthetic carbon, synthetic adsorbent, or inorganic molecular sieve.

15. The process of claim 1 wherein said adsorbent is a combination of two or more activated carbons.

16. The process of claim 13 wherein said adsorbent comprises at least one activated carbon having pore surface area of from about 1000 to about 2000 $m^2/g$.

17. The process of claim 16 wherein said activated carbon has a pore surface area of from about 1400 to about 1800 $m^2/g$.

18. The process of claim 1 wherein said second porous material has a pore volume of about 1 to about 1.2 ml/g.

19. The process of claim 1 wherein said first porous material has a pore volume of about 0.1 to about 0.5 ml/g.

20. The process of claim 1 wherein said first porous material has a pore volume of about 0.15 to about 0.4 ml/g.

21. The process of claim 13 wherein said adsorbent comprises at least one activated carbon having a trace capacity number of 16 mg/cc or greater, and an iodine number of about 850 mg/g or greater.

22. A process for producing a high purity organic solvent from crude $C_1$-$C_3$ alcohol comprising:
provided a stream of crude $C_1$-$C_3$ alcohol which fails to satisfy one or more of the following absorption criteria: a UV absorption for a 5 cm cell of less than about 0.8 AUFS at 225 nm, less than about 0.1 AUFS at 250 nm, and less than about 0.025 AUFS at 300 and 400 nm, a Tennessee-Eastman absorbance of less than about 0.0050 AUFS at 220 nm and a Tennessee-Eastman absorbance less than about 0.0010 AUFS at 254 nm;
adsorbing at least one impurity contained in said crude $C_1$-$C_3$ alcohol onto an adsorbent comprising a first porous material having a pore volume from about 0.1 to about 0.8 ml/g and a second porous material having a pore volume from about 1.0 to about 1.5 ml/g, wherein said first and second porous materials are independently selected from the group consisting of activated carbons, synthetic carbons, synthetic adsorbents, and inorganic molecular sieves ;
storing said adsorbent solvent product in a storage container; and
distilling said adsorbent solvent product to produce purified $C_1$-$C_3$ alcohol which meets the following criteria: a UV absorption for a 5 cm cell of less than about 1.0 AUFS at 225 nm, less than about 0.3 AUFS at 250 nm, less than about 0.05 AUFS at 300 and 400 nm, a Tennessee-Eastman absorbance of less than about 0.0090 AUFS at 220 nm and a Tennessee-Eastman absorbance of less than about 0.0050 AUFS at 254 nm.

23. The process of claim 1 wherein said UV absorbing impurity has a UV absorbance greater than a UV absorbance of said organic solvent.

24. The process of claim 1 further comprising the step of:
distilling said organic solvent after said adsorbing step, wherein said adsorbing step and said distilling step together produce a purified organic solvent comprising a second amount of UV absorbing impurities, the second amount of impurities being less than the first amount of impurities.

25. The process of claim 1 wherein said organic solvent is methanol.

* * * * *